(12) United States Patent
Flohr et al.

(10) Patent No.: US 11,406,751 B2
(45) Date of Patent: Aug. 9, 2022

(54) DETERMINATION OF A TIME-DEPENDENT CONTRAST AGENT INJECTION CURVE AS A FUNCTION OF CT SCAN PARAMETERS

(71) Applicants: Siemens Aktiengesellschaft, Munich (DE); Bayer Pharma Aktiengesellschaft

(72) Inventors: Thomas Flohr, Uehlfeld (DE); Gregor Jost, Berlin (DE); Hubertus Pietsch, Kleinmachnow (DE)

(73) Assignees: SIEMENS AKTIENGESELLSCHAFT, Munich (DE); BAYER PHARMA AKTIENGESELLSCHAFT, Berlin (DE)

(*) Notice: Subject to any disclaimer, the term of this patent is extended or adjusted under 35 U.S.C. 154(b) by 481 days.

(21) Appl. No.: 15/138,501

(22) Filed: Apr. 26, 2016

(65) Prior Publication Data

US 2016/0325040 A1 Nov. 10, 2016

(30) Foreign Application Priority Data

May 4, 2015 (DE) .......................... 102015208202.4

(51) Int. Cl.
*A61M 5/00* (2006.01)
*A61B 6/00* (2006.01)
(Continued)

(52) U.S. Cl.
CPC ............. *A61M 5/007* (2013.01); *A61B 6/032* (2013.01); *A61B 6/481* (2013.01); *A61B 6/486* (2013.01);
(Continued)

(58) Field of Classification Search
None
See application file for complete search history.

(56) References Cited

U.S. PATENT DOCUMENTS 8,208,699 B2 * 6/2012 Hay ....................... A61B 6/469
378/8
9,501,620 B2 * 11/2016 Okell ..................... A61B 6/507
(Continued)

FOREIGN PATENT DOCUMENTS

| CN | 101277648 A | 10/2008 |
|----|-------------|---------|
| CN | 103313658 A | 9/2013  |
| CN | 104125841 A | 10/2014 |

OTHER PUBLICATIONS

German Office Action dated Jan. 26, 2016.
(Continued)

*Primary Examiner* — Shahdeep Mohammed
(74) *Attorney, Agent, or Firm* — Harness, Dickey & Pierce, P.L.C.

(57) ABSTRACT

A method for the automatic determination of a contrast agent protocol for a contrast agent-enhanced medical imaging method is described. The method includes an overview recording of a region of interest of an object under examination. In addition, an image recording protocol including a plurality of recording parameters is defined on the basis of the overview recording. Furthermore, recording time points are determined for a plurality of z-positions of the region of interest on the basis of the image recording protocol. In addition, the structures acquired with the overview recording are assigned to the recording time points determined. Finally, a contrast agent protocol including the temporal course of a contrast agent injection curve is defined as a function of the acquired structures and the assigned recording time points. A contrast agent protocol determination device is also described, as well as an imaging medicinal device.

24 Claims, 3 Drawing Sheets

(51) Int. Cl.
*A61B 6/03* (2006.01)
*G01R 33/56* (2006.01)

(52) U.S. Cl.
CPC .............. *A61B 6/488* (2013.01); *A61B 6/503* (2013.01); *A61B 6/504* (2013.01); *G01R 33/5601* (2013.01); *A61B 6/469* (2013.01); *A61B 6/5217* (2013.01); *A61B 6/541* (2013.01); *A61M 2205/3334* (2013.01); *A61M 2230/04* (2013.01)

(56) References Cited

U.S. PATENT DOCUMENTS

| | | | |
|---|---|---|---|
| 2004/0082846 A1* | 4/2004 | Johnson | A61B 5/02014 |
| | | | 600/410 |
| 2010/0249582 A1* | 9/2010 | Feuerlein | A61B 6/504 |
| | | | 600/431 |
| 2012/0134464 A1* | 5/2012 | Hoernig | A61B 6/481 |
| | | | 378/22 |
| 2013/0101079 A1* | 4/2013 | Hough | A61B 6/545 |
| | | | 378/8 |
| 2013/0253895 A1 | 9/2013 | Okell et al. | |
| 2014/0018672 A1* | 1/2014 | Klahr | A61B 6/032 |
| | | | 600/425 |
| 2014/0364720 A1* | 12/2014 | Darrow | A61B 5/748 |
| | | | 600/410 |
| 2015/0039553 A1 | 2/2015 | Becker et al. | |
| 2015/0080707 A1* | 3/2015 | Carmi | A61B 8/06 |
| | | | 600/415 |
| 2015/0199121 A1* | 7/2015 | Gulaka | A61B 6/463 |
| | | | 715/771 |

OTHER PUBLICATIONS

Chinese Office Action for corresponding Application No. 2016102870501 dated Sep. 28, 2018 and partial English translation thereof.
Second Chinese Office Action for corresponding Application No. 2016102870501, dated May 23, 2019, partial English translation thereof.
Chinese Rejection Decision for corresponding Application No. 2016102870501, dated Apr. 20, 2020.

* cited by examiner

DETERMINATION OF A TIME-DEPENDENT CONTRAST AGENT INJECTION CURVE AS A FUNCTION OF CT SCAN PARAMETERS

PRIORITY STATEMENT

The present application hereby claims priority under 35 U.S.C. §119 to German patent application number DE 102015208202.4 filed May 4, 2015, the entire contents of which are hereby incorporated herein by reference.

FIELD

At least one embodiment of the invention generally relates to a method for the determination of a time-dependent contrast agent injection curve as a function of CT scan parameters. At least one embodiment of the invention also generally relates to a method for performing imaging of a region of interest of an object under examination. At least one embodiment of the invention further generally relates to a contrast agent injection curve determination device. Finally, at least one embodiment of the invention relates to a computed tomography system.

BACKGROUND

Modern imaging methods are used to generate two- or three-dimensional image data which can be used to visualize an imaged object under examination and also additionally for further applications.

Imaging methods are frequently based on the acquisition of X-rays, wherein so-called projection measured data is generated. For example, projection measured data can be acquired via a computed tomography system (CT systems). With CT systems, usually a combination of an X-ray source and an oppositely arranged X-ray detector arranged on a gantry rotate about measuring chamber in which the object under examination (which will hereinafter be referred to without restricting the generality as the patient). In this case, the center of rotation (also called the "isocenter") coincides with a so-called system axis z. The patient is irradiated with X-rays from the X-ray source during one or more cycles, wherein projection measured data or X-ray projection data is acquired via the opposite X-ray detector.

The X-ray detectors used for CT imaging generally have a plurality of detection units which are usually arranged in the form of a regular pixel array. The detection units in each case generate a detection signal for the incident X-rays on the detection units with said signal being analyzed at specific time points with respect to the intensity and spectral distribution of the X-rays in order to obtain conclusions regarding the object under examination and to generate projection measured data.

When visualizing functional relationships and structures of patients' bodies, so-called contrast agents are used during medical imaging. During contrast agent-enhanced medical imaging, it is necessary to ensure that the contrast agent is also present in the desired concentration in the region of interest of the patient's body at the time point of the imaging. One possibility for visualizing the distribution of the contrast agent in the body consists in the performance of a so-called bolus-tracking scan (BT scan for short) or a so-called test-bolus scan.

In both cases, an attenuation value in a larger vessel, for example the aorta, is measured as a function of the time following the commencement of the contrast agent injection and the imaging is started as soon as the attenuation value exceeds a specific threshold. With this procedure, both the parameters of the CT imaging, such as, for example, the feed rate, and the parameters of the contrast agent injection, such as, for example, the concentration, the amount of the contrast agent and the flow rate are fixed during the CT imaging and are also not changed. With this procedure, it is not possible to predict how the contrast will develop at different times at different positions in the patient to be examined during the CT imaging.

In particular in the case of CT angiography, the contrast agent protocol relating to the concentration and amount of the contrast agent and the flow rate and the CT examination protocol must be well matched in order to achieve sufficient contrast for all vessels of interest during the imaging. Particularly with modern multi-line CT devices with high-speed rotation facilitating a feed rate during the examination, it can happen that the imaging overtakes the contrast agent bolus, such as, can, for example, be the case with an angiography of the legs. Since the flow rate of the blood changes as a function of the anatomical position and the diameter of the vessels, the speed of the contrast agent bolus also changes as a function of place and time. With conventional matching by way of a test bolus or bolus tracking, normally only an optimum starting time for the CT imaging is determined, but there is no temporal matching of the contrast during the course of the imaging. Hence, this results in non-optimum contrast at least in subareas of a region to be imaged of an object under examination.

SUMMARY

At least one embodiment of the present invention achieves a contrast with an approximately uniform quality during contrast agent-enhanced imaging, in particular contrast agent-enhanced CT imaging, during the entire imaging process and in all subareas to be recorded.

At least one embodiment is directed to a method for the automatic determination of a contrast agent protocol for a contrast agent-enhanced medical imaging method; at least one embodiment is directed to an imaging method; at least one embodiment is directed to a contrast agent curve determination device; and at least one embodiment is directed to an imaging medicinal device.

With the method according to at least one embodiment of the invention for the automatic determination of a contrast agent protocol for a contrast agent-enhanced medical imaging method, initially an overview recording of a region of interest of an object under examination is performed. The overview recording can be used to determine the precise position of the object under examination and the positions of individual structures to be imaged, such as, for example, organs or blood vessels. During the further course of the method, this information is used to match the imaging and the contrast agent administration to one another.

In addition, an image recording protocol comprising a plurality of recording parameters is defined on the basis of the overview recording. In addition, recording time points are determined for a plurality of z-positions of the region of interest on the basis of the image recording protocol. The image recording protocol contains definitions for the scheduling of the temporal course of the planned imaging.

These definitions can be used to assign recording time points to individual positions in the region to be imaged. Then, the recording time points determined are assigned to individual structures acquired during the overview recording. Following the assignment, the recording time point for each of the structures is known.

Finally, a contrast agent protocol comprising the temporal course of a contrast agent injection curve is defined as a function of the acquired structures and the assigned recording time points. The definitions take account of the effects of the individual structures on the distribution and concentration of the contrast agent so that an optimum distribution and concentration of the contrast agent at the respective recording time points in the assigned structures to be imaged prevails.

A contrast agent injection curve should be understood to mean a graphical depiction of the flow of the contrast agent as a function of time at the injection site of the contrast agent. The flow of the contrast agent can for example designate a quantity of a contrast agent injected in each time unit.

The contrast agent protocol determination device according to at least one embodiment of the invention for the automatic determination of a contrast agent protocol for a contrast agent-enhanced medical imaging method comprises a raw data acquisition unit for recording raw data for an overview recording of a region of interest of an object under examination. It also comprises an image data reconstruction unit for the reconstruction of image data from the raw data acquired. The contrast agent protocol determination device also includes an image recording protocol defining unit for defining an image recording protocol comprising a plurality of recording parameters.

The contrast agent protocol determination device according to at least one embodiment of the invention also comprises a recording time point determining unit for the determination of a recording time unit for each z-position of the region of interest. The contrast agent protocol determination device also comprises an assignment unit for the assignment of structures acquired during the overview recording to the recording time points determined.

Finally, the contrast agent protocol determination device according to at least one embodiment of the invention also comprises a contrast agent protocol defining unit for defining the contrast agent protocol comprising the temporal course of a contrast agent injection curve as a function of the acquired structures and the assigned recording time points.

The imaging medicinal device according to at least one embodiment of the invention, preferably a computed tomography system, comprises a control device and the contrast agent protocol determination device according to at least one embodiment of the invention.

The contrast agent protocol determination device according to at least one embodiment of the invention can, for example, be part of the control device; however, it can also be arranged separately from the control device if, for example, a conventional control device is to be used for the application of the method according to at least one embodiment of the invention.

The components of the contrast agent curve determination device according to at least one embodiment of the invention can be predominantly embodied in the form of software components. This in particular relates to the image data reconstruction unit, the image recording protocol defining unit, the recording time point determining unit, the assignment unit and the contrast agent protocol defining unit. However, in principle, these components can to some extent, in particular when particularly quick calculations are concerned, also be implemented in the form of software-supported hardware, for example FPGAs or the like. Similarly, for example when only the acceptance of data from other software components is concerned, the required interfaces can be embodied as software interfaces. However, they can also be embodied as hardware-based interfaces controlled via suitable software.

An extensively software-based implementation has the advantage that it is also possible to retrofit control devices used to date in a simple way via a software update in order to work in the manner according to at least one embodiment of the invention.

At least one embodiment is directed to a corresponding computer program product with a computer program which can be loaded directly into a memory device of a control device of an imaging system, preferably computed tomography system, including program segments in order to carry out all the steps of the method according to at least one embodiment of the invention when the program is executed in the control device. In addition to the computer program, a computer program product of this kind can optionally comprise additional parts such as, for example, documentation and/or additional components and also hardware components, such as, for example, hardware keys (dongles etc.) for using the software.

Transportation to the control device and/or storage on or in the control device of at least one embodiment can take place via a computer-readable medium, for example a memory stick, a hard disk or another kind of transportable or integrated data carrier on which the program segments of the computer program which can be read-in and executed by a computing unit of the control device are stored. To this end, the computing unit can, for example, comprise one or more interacting microprocessors or the like.

The dependent claims and the subsequent description each contain particularly advantageous embodiments and developments of the invention. Here, in particular the claims of one claim category can be developed analogously to the dependent claims of another claim category. In addition, it is also possible within the context of the invention for the different features of different example embodiments to be combined and claims to be combined to form new example embodiments.

BRIEF DESCRIPTION OF THE DRAWINGS

The invention will be described once again below with reference to the attached figures and to example embodiments. The figures show.

DETAILED DESCRIPTION OF THE EXAMPLE EMBODIMENTS

Figure 1:
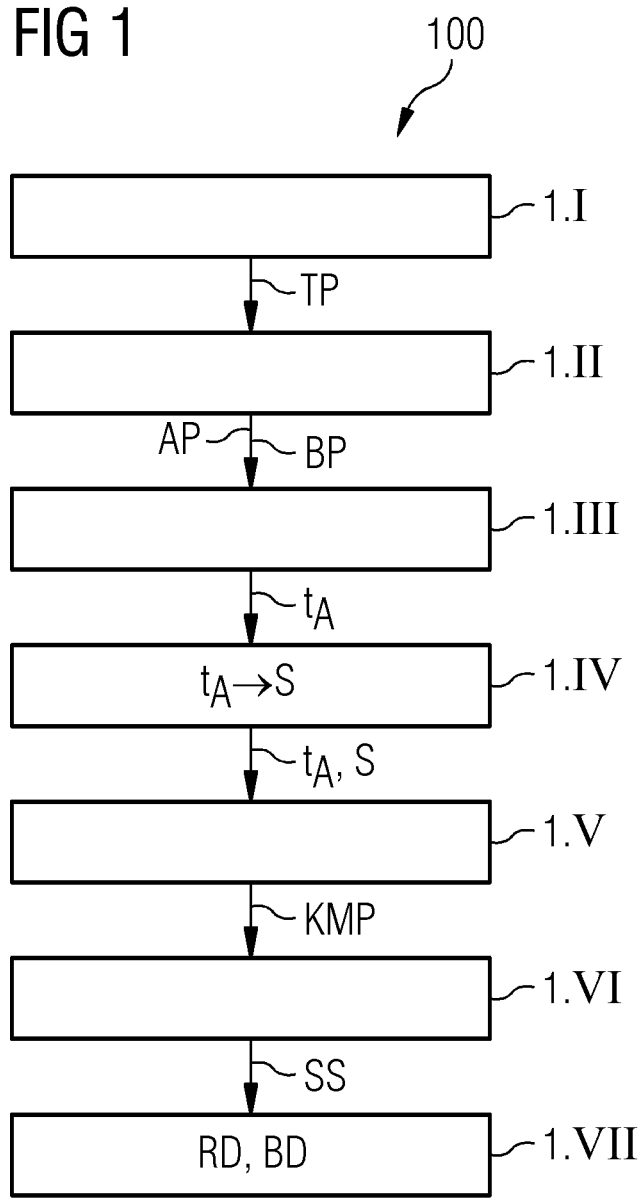
FIG. 1 a flow diagram illustrating a method for the automatic determination of a contrast agent protocol for a contrast agent-enhanced medical imaging method according to an example embodiment of the invention, FIG. 2 a schematic depiction of a contrast agent protocol determination device according to an example embodiment of the invention, FIG. 3 a computed tomography system with a contrast agent protocol determination device according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

With the method according to at least one embodiment of the invention for the automatic determination of a contrast agent protocol for a contrast agent-enhanced medical imaging method, initially an overview recording of a region of interest of an object under examination is performed. The overview recording can be used to determine the precise position of the object under examination and the positions of individual structures to be imaged, such as, for example, organs or blood vessels. During the further course of the method, this information is used to match the imaging and the contrast agent administration to one another.

In addition, an image recording protocol comprising a plurality of recording parameters is defined on the basis of the overview recording. In addition, recording time points are determined for a plurality of z-positions of the region of interest on the basis of the image recording protocol. The image recording protocol contains definitions for the scheduling of the temporal course of the planned imaging.

These definitions can be used to assign recording time points to individual positions in the region to be imaged. Then, the recording time points determined are assigned to individual structures acquired during the overview recording. Following the assignment, the recording time point for each of the structures is known.

Finally, a contrast agent protocol comprising the temporal course of a contrast agent injection curve is defined as a function of the acquired structures and the assigned recording time points. The definitions take account of the effects of the individual structures on the distribution and concentration of the contrast agent so that an optimum distribution and concentration of the contrast agent at the respective recording time points in the assigned structures to be imaged prevails.

A contrast agent injection curve should be understood to mean a graphical depiction of the flow of the contrast agent as a function of time at the injection site of the contrast agent. The flow of the contrast agent can for example designate a quantity of a contrast agent injected in each time unit.

With the imaging method according to at least one embodiment of the invention for a contrast agent-enhanced depiction of a region to be imaged of an object under examination, the method according to at least one embodiment of the invention for the determination of a contrast agent protocol is applied and then imaging is performed by way of a contrast agent-enhanced medical imaging method using the contrast agent protocol determined. For example, the contrast agent-enhanced medical imaging method can be a contrast agent-enhanced CT imaging method.

The contrast agent protocol determination device according to at least one embodiment of the invention for the automatic determination of a contrast agent protocol for a contrast agent-enhanced medical imaging method comprises a raw data acquisition unit for recording raw data for an overview recording of a region of interest of an object under examination. It also comprises an image data reconstruction unit for the reconstruction of image data from the raw data acquired. The contrast agent protocol determination device also includes an image recording protocol defining unit for defining an image recording protocol comprising a plurality of recording parameters.

The contrast agent protocol determination device according to at least one embodiment of the invention also comprises a recording time point determining unit for the determination of a recording time unit for each z-position of the region of interest. The contrast agent protocol determination device also comprises an assignment unit for the assignment of structures acquired during the overview recording to the recording time points determined.

Finally, the contrast agent protocol determination device according to at least one embodiment of the invention also comprises a contrast agent protocol defining unit for defining the contrast agent protocol comprising the temporal course of a contrast agent injection curve as a function of the acquired structures and the assigned recording time points.

The imaging medicinal device according to at least one embodiment of the invention, preferably a computed tomography system, comprises a control device and the contrast agent protocol determination device according to at least one embodiment of the invention.

The contrast agent protocol determination device according to at least one embodiment of the invention can, for example, be part of the control device; however, it can also be arranged separately from the control device if, for example, a conventional control device is to be used for the application of the method according to at least one embodiment of the invention.

The components of the contrast agent curve determination device according to at least one embodiment of the invention can be predominantly embodied in the form of software components. This in particular relates to the image data reconstruction unit, the image recording protocol defining unit, the recording time point determining unit, the assignment unit and the contrast agent protocol defining unit. However, in principle, these components can to some extent, in particular when particularly quick calculations are concerned, also be implemented in the form of software-supported hardware, for example FPGAs or the like. Similarly, for example when only the acceptance of data from other software components is concerned, the required interfaces can be embodied as software interfaces. However, they can also be embodied as hardware-based interfaces controlled via suitable software.

An extensively software-based implementation has the advantage that it is also possible to retrofit control devices used to date in a simple way via a software update in order to work in the manner according to at least one embodiment of the invention.

At least one embodiment is directed to a corresponding computer program product with a computer program which can be loaded directly into a memory device of a control device of an imaging system, preferably computed tomography system, including program segments in order to carry out all the steps of the method according to at least one embodiment of the invention when the program is executed in the control device. In addition to the computer program, a computer program product of this kind can optionally comprise additional parts such as, for example, documentation and/or additional components and also hardware components, such as, for example, hardware keys (dongles etc.) for using the software.

Transportation to the control device and/or storage on or in the control device of at least one embodiment can take place via a computer-readable medium, for example a memory stick, a hard disk or another kind of transportable or integrated data carrier on which the program segments of the computer program which can be read-in and executed by a computing unit of the control device are stored. To this end, the computing unit can, for example, comprise one or more interacting microprocessors or the like.

In one embodiment of the method according to at least one embodiment of the invention for the automatic determination of a contrast agent protocol for a contrast agent-enhanced medical imaging method, the medical imaging method comprises a magnetic resonance imaging method or alternatively a computed tomography method.

Preferably, with the method according to at least one embodiment of the invention for the automatic determination of a contrast agent protocol for a contrast agent-enhanced medical imaging method, the definition of the contrast agent protocol includes the definition of the flow rate of an injected contrast agent as a function of time. The temporal control of the flow rate enables the amount of contrast agent and the concentration of contrast agent to be controlled at specific times at specific positions in the body of a patient to be examined.

Alternatively or additionally, the definition of the contrast agent protocol includes the definition of the concentration of an injected contrast agent as a function of time. The temporal control of the concentration of the contrast agent during injection can also be used to control the amount of contrast agent and the concentration of contrast agent at specific times at specific positions in the body of a patient to be examined.

In a particularly preferred variant of the method according to at least one embodiment of the invention for the automatic determination of a contrast agent protocol for a contrast agent-enhanced medical imaging method, the parameters of the image recording protocol include the size of the region to be imaged. If the position and the size of a region to be imaged are known and if these are taken into account during the contrast agent administration by temporal control of the amount of contrast agent, it is possible to define the time point at which the depiction of the region to be imaged starts and a corresponding time point for contrast agent administration and the required amount of contrast agent as a function of time in order to achieve optimum contrast of the region to be imaged.

It is also advantageous if, in the event of the imaging system being a CT system, the parameters of the image recording protocol comprise the rotation time of the CT system. Particularly advantageously, the parameters of the image recording protocol comprise the collimation of the X-ray beam. In addition, the parameters of the image recording protocol can comprise a spiral pitch of the CT system. The named parameters provide information on the speed at which CT imaging is performed. It is very useful to know these parameters in order to be able to determine the temporal course of CT imaging. If the temporal course of the CT imaging is known, it can be synchronized with the contrast agent administration, wherein the contrast agent administration is organized as a function of time in the way described above.

The method according to at least one embodiment of the invention for the automatic determination of a contrast agent protocol for a contrast agent-enhanced medical imaging method enables the definition of the contrast agent protocol to take account of empirical data, which preferably includes typical times of arrival of the contrast agent in individual organs or vessels of a patient collective. Taking into account this information in particular enables the dispersion of the contrast agent and its concentration in the patient to be examined as a function of time to be predicted more precisely.

In order to be able to predict the concentration and the amount of the contrast agent in a region to be imaged, it is advantageous for a model describing the circulatory parameters of the object under examination to be taken into account during the definition of the contrast agent protocol. For example, the circulation parameters point to conclusions relating to the flow rate of the blood, which can in turn be used to calculate times of arrival of the contrast agent in different structures to be imaged.

The behavior of the contrast agent in the body of the object under examination can be predicted particularly precisely if the model takes account of the fact that the flow rate of the blood changes as a function of the anatomical position and the diameter of the blood vessels through which the blood flows.

With the method according to at least one embodiment of the invention for the automatic determination of a contrast agent protocol for a contrast agent-enhanced medical imaging method, the definition of the contrast agent protocol can comprise the definition of the mixing ratio of a contrast agent with a saline chaser as a function of the anatomy of the object under examination. A saline chaser is a saline solution, for example a sodium chloride solution, which can be mixed with the contrast agent. The addition of the saline solution can be used to influence the concentration of the contrast agent at different time points at different positions.

In one embodiment of the imaging method according to at least one embodiment of the invention, following the determination of the contrast agent protocol, a control signal for controlling a contrast agent injection is sent to a contrast agent injection device, wherein the control signal according to the contrast agent protocol determined is generated. I.e., the contrast agent injection device is controlled on the basis of the contrast agent protocol determined.

FIG. 1 is a flow diagram illustrating a method 100 for contrast agent-enhanced imaging according to an example embodiment of the invention. The method is described in connection with contrast agent-enhanced imaging via a CT system, but is not restricted thereto. In step 1.I of the method 100, initially a topogram TP of a region of interest of a patient is recorded. The topogram TP can, for example, be used to determine the position of the patient and the position and the dimensions of individual body regions to be examined.

Then, a CT examination protocol BP is defined in step 1.II. The CT examination protocol BP for example defines a region to be imaged VOI of a patient's body, also called a scan region. Also defined therein are so-called scan parameters AP, such as, for example, the rotation time of the rotating system comprising an X-ray source or X-ray tube and a detector of the CT system, the collimation of X-rays of the CT system and a spiral pitch P. The spiral pitch P is described as follows:

$$P = \frac{d}{M \cdot S}, \quad (1)$$

wherein d represents the feed for the region to be imaged VOI for each 360° X-ray tube cycle, M designates the number of detector lines acquired simultaneously, i.e. the beam collimation, and S symbolizes the slice thickness selected.

In step 1.III, recording time points $t_A$ for a plurality of z-positions of the region of interest VOI are determined on the basis of the CT examination protocols. It is possible to determine unequivocally from the CT examination protocol and the topogram TP acquired in step 1.I which subarea of the region to be imaged VOI, when viewed in the z-direction, will Be acquired as an image at which time point $t_A$. In step 1.IV, the structures S present in the individual subareas, for example organs, blood vessels or the like, are assigned to the imaging time points $t_A$.

In step 1.V, a contrast agent injection curve is now defined as a function of the present structures and the assigned imaging time points $t_A$. I.e., the parameters of the contrast agent injection are selected in a time-dependent or time-varying manner such that optimum contrast is achieved in the individual structures at the respective imaging time point $t_A$. The structures present can be assigned an anatomical position. The linking of the anatomical position and the time point $t_A$ at which it is reached during the imaging with the temporal change to the parameters of the contrast agent injection can, for example, be performed on an empirical basis. The empirically acquired data can, for example, be obtained from a previous examination of typical times of arrival of the contrast agent in the individual organs or vessels in a patient collective.

Alternatively or additionally, the changes to the parameters of the contrast agent injection can also be based on a complex model in that, for example, circulatory parameters of the patient are also taken into account. One example of a structure is the region of the aorta in which the aorta divides into the iliac arteries. At this position, also called the bifurcation, with a conventional procedure, the contrast agent concentration is lower than desired. Therefore, when the protocol is defined, the contrast agent injection is set and the time of a higher contrast agent flow rate established such that, at the time point $t_A$ at which the bifurcation is imaged, the contrast agent concentration in the region of the bifurcation reaches a sufficient, or preferably optimum, value.

In step 1.VI, a control signal SS is sent to a contrast agent injection device 25 (see FIG. 3) with which a contrast agent flow or a contrast agent flow density is controlled. Finally, in step 1.VII, the imaging of the region to be imaged VOI of the patient is now performed with optimized contrast. With this imaging, initially, as usual, raw data RD is acquired and image data BD reconstructed therefrom.

Figure 2:
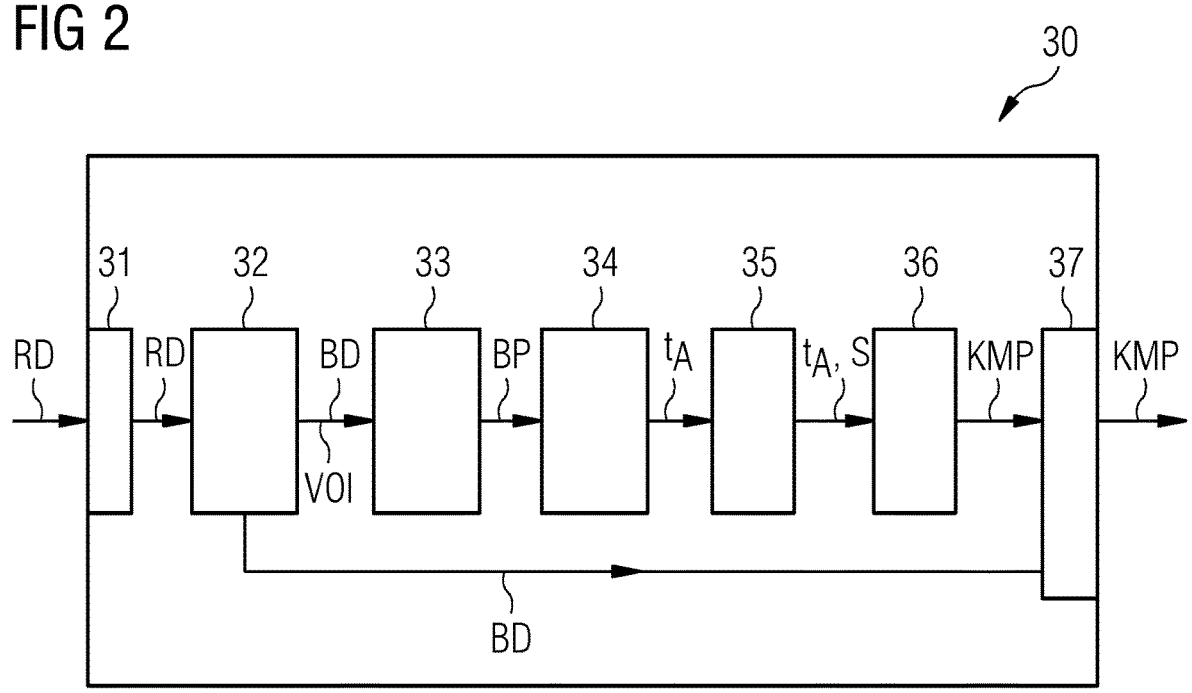

FIG. 2 illustrates a contrast agent protocol determination device 30 according to an example embodiment of the invention. The contrast agent protocol determination device 30 comprises a raw data acquisition unit 31. The raw data acquisition unit 31 acquires raw data RD, for example for an overview recording of a region of interest VOI of an object under examination O. The raw data RD acquired is transferred to an image data reconstruction unit 32, which reconstructs image data BD from the raw data RD acquired. The reconstructed image data BD is transferred to an image recording protocol defining unit 33, which defines an image recording protocol BP comprising a plurality of recording parameters or scan parameters. In addition, the image data BD is also transferred to an output interface 37, from which it is, for example, forwarded to a storage unit 22 (see FIG. 3).

The image recording protocol BP defined is transferred to a recording time point determining unit 34, which determines a recording time point $t_A$ for each z-position of the region of interest VOI on the basis of the image recording protocol BP received. The recording time points determined $t_A$ are transferred to an assignment unit 35, which assigns structures S acquired during the overview recording to the recording time points determined $t_A$. The assignments determined are transferred to a contrast agent protocol defining unit 36, which defines a contrast agent protocol KMP. The contrast agent protocol KMP defines the temporal course of a contrast agent injection curve KM as a function of the structures acquired during the overview recording S and the assigned recording time points $t_A$. The contrast agent protocol KMP determined is then transferred to the aforementioned output interface from which it is, for example, forwarded to a memory unit 22 (see FIG. 3).

Figure 3:
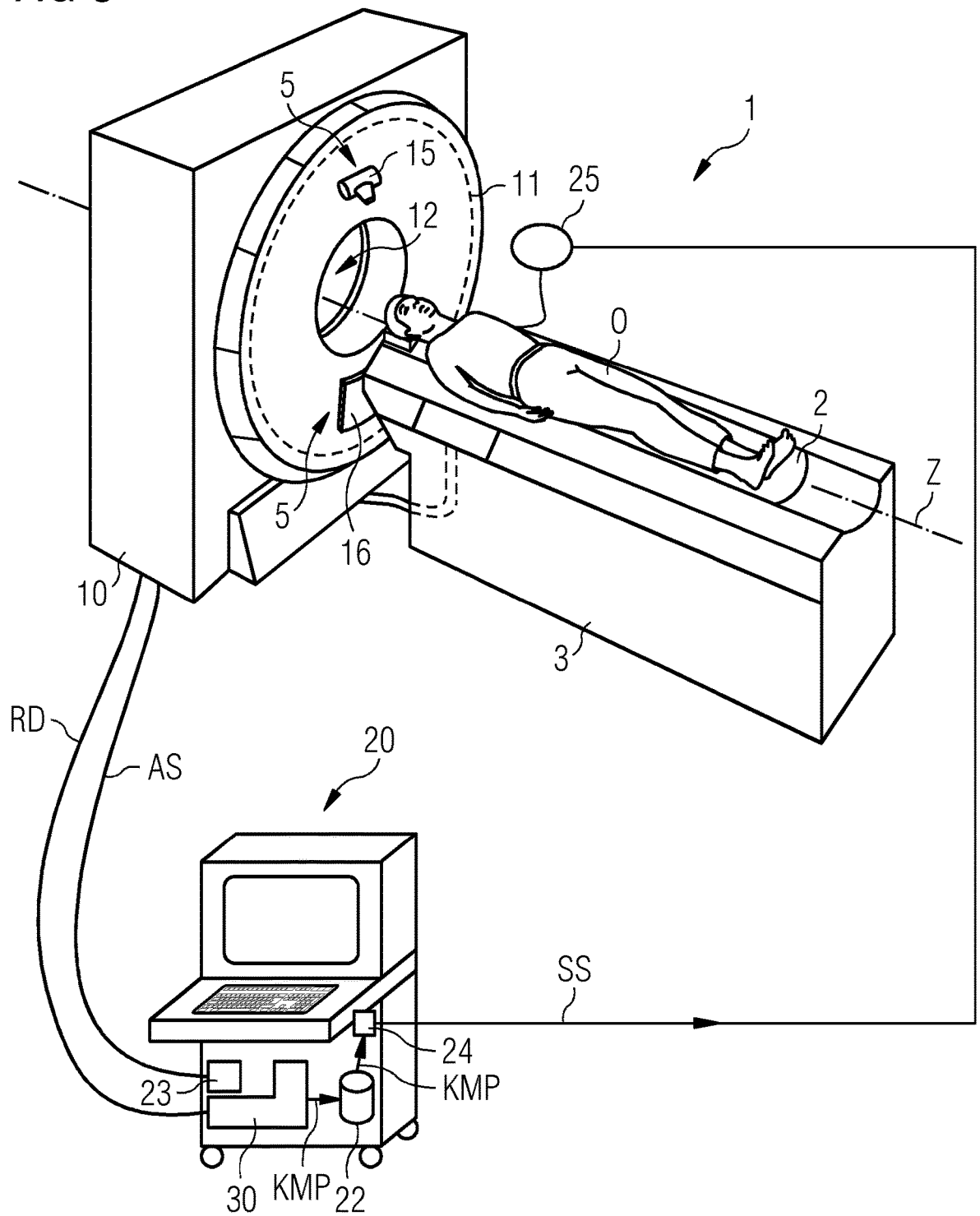

FIG. 3 shows a computed tomography system 1 according to an example embodiment of the invention, which also comprises a contrast agent protocol determination device 30 corresponding to the arrangement shown in FIG. 2. In this case, the CT system 1 substantially comprises a usual scanner 10, in which a projection data acquisition unit 5 with a detector 16 and an X-ray source 15 lying opposite to the detector 16 on a gantry 11 rotates about a measuring chamber 12. Located before the scanner 10, there is a patient support device 3 or a patient table 3 the upper part 2 of which with a patient O lying thereon can be pushed toward the scanner 10 in order to move the patient O through the measuring chamber 12 relative to the detector system 16. The scanner 10 and the patient table 3 are controlled by a control device 20 which emits acquisition control signals AS via a usual control interface 23 in order to control the entire system according to predetermined measurement protocols in the conventional manner.

In the case of spiral acquisition, a movement of the patient O along the z-direction corresponding to the longitudinal system axis z through the measuring chamber 12 and the simultaneous circulation of the X-ray source 15 produces a helical path for the X-ray source 15 relative to the patient O during the measurement. Parallel thereto, the detector 16 the detector always rotates opposite to the X-ray source 15 in order to acquire projection measured data RD, which is then used for the reconstruction of volume and/or slice image data. It is also possible to carry out a sequential measuring method, for example for recording an individual slice in which a fixed position in z-direction is approached and then during one cycle, a partial cycle or a plurality of cycles, the required projection measured data RD is acquired at the relevant z-position in order to reconstruct a sectional view at this z-position or to reconstruct image data BD from the projection data for a plurality of z-positions. The method 100 according to the invention can, in principle, also be used on other CT systems, for example with a plurality of X-ray sources and/or detectors and/or with a detector forming a complete ring.

The projection measured data RD acquired by the detector 16 (hereinafter also called raw data RD) is transferred via a raw data interface 31 (see FIG. 2), also called a raw data acquisition unit, which is part of the contrast agent protocol determination device 30 according to the invention, to the control device 20. This raw data RD is then, optionally following suitable preprocessing (for example filtering and/or beam hardening correction), further processed in an image reconstruction unit 32 (see FIG. 2), which in this example embodiment is implemented in the control device 20 in the form of software on a processor. This image reconstruction unit reconstructs image data BD on the basis of the raw data RD by way of a reconstruction method. The reconstruction method used can, for example, be a reconstruction method based on filtered back projection.

If the reconstructed image data is image data from an overview image, this image data BD is then further processed within the control device 20 via the contrast agent protocol determination device 30 as was explained in detail in connection with FIG. 2, and a contrast agent protocol KMP is determined. The control device 20 then starts the actual contrast agent-enhanced imaging using corresponding acquisition control signals AS and using the contrast agent protocol KMP.

The acquired image data BD is stored in a memory 22 of the control device 20 and/or output in the usual way on the screen of the control device 20. It can also be fed via an interface not shown in FIG. 3 into a network connected to the computed tomography system 1, for example a radiology information system (RIS), and stored in a bulk storage device, which can be accessed in-situ, or output as images on printers or filming stations connected thereto. Hence, the data can be further processed as desired and then stored or output.

In addition, FIG. 3 also shows a contrast agent injection device 25 with which the patient O can be injected with a contrast agent, which, for example, is used for imaging a vessel or a vascular system via the computed tomography system 1. The contrast agent injection device 25 is controlled by the control device 20 via a signal SS so that the patient O is injected with a contrast agent according to the contrast agent protocol KMP determined. For this purpose, the control device 20 comprises an actuation unit 24. The actuation unit 24 generates the control signal SS on the basis of the contrast agent protocol KMP, which is, for example, stored temporarily in the memory 22.

Finally, reference is again made to the fact that the above-described method 100, the contrast agent protocol determination device 30 described and the computed tomography system 1 described are only preferred example embodiments of the invention and that the invention can be varied by the person skilled in the art without departing from the scope of invention as specified by the claims. For example, the imaging system used can also be a magnetic resonance tomography system. For purposes of completeness, reference is also made to the fact that the use of the indefinite article "a" or "an" does not preclude the possibility that the features in question may also be present on a multiple basis. Similarly, the term "unit" does not preclude the possibility that the unit comprises a plurality of components, which could also be spatially distributed.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. §112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatically defining a contrast agent protocol for a contrast agent-enhanced medical imaging method, the method comprising:

performing, prior to injecting a contrast agent, an overview recording of a region of interest of an object under examination via a medical imaging device;

defining an image recording protocol based on image data recorded during the overview recording, the image recording protocol including a plurality of recording parameters including at least a scan rate of the medical imaging device;

determining, prior to injecting the contrast agent, recording time points based on the image recording protocol, the recording time points being for a plurality of z-positions of the region of interest;

assigning structures to the determined recording time points prior to injecting the contrast agent, the structures being acquired from the overview recording, the structures including at least one of an organ and a blood vessel; and automatically defining, prior to injecting the contrast agent, the contrast agent protocol, including syncing administering the contrast agent as a function of the scan rate, the acquired structures and respectively assigned recording time points to the assigned structures, wherein the contrast agent protocol including a temporal course of a contrast agent injection curve is defined as the function of the acquired structures and assigned recording time points.

2. The method of claim 1, wherein the automatically defining the contrast agent protocol includes a definition of a mixing ratio of the contrast agent with a saline chaser as a function of anatomy of the object under examination.

3. The method of claim 1, wherein the automatically defining the contrast agent protocol includes a definition of a flow rate of an injected contrast agent as a function of time, a definition of a concentration of an injected contrast agent as a function of time, or both a definition of a flow rate of an injected contrast agent as a function of time and a definition of a concentration of an injected contrast agent as a function of time.

4. The method of claim 3, wherein the medical imaging device is a CT system, and wherein the plurality of recording parameters of the image recording protocol include a rotation time of the CT system, a collimation of an X-ray beam, a spiral pitch of the CT system, a subcombination thereof, or a combination thereof.

5. The method of claim 1, wherein the plurality of recording parameters of the image recording protocol include a size of the region of interest to be imaged.

6. The method of claim 5, wherein the medical imaging device is a CT system, and wherein the plurality of recording parameters of the image recording protocol include a rotation time of the CT system, a collimation of an X-ray beam, a spiral pitch of the CT system, a subcombination thereof, or a combination thereof.

7. The method of claim 1, wherein the automatically defining the contrast agent is based on empirical data, derived from collective of data, including arrival time of the contrast agent in one or more structures.

8. The method of claim 7, wherein the empirical data includes typical times of arrival of the contrast agent in individual organs or vessels of the object under examination.

9. The method of claim 1, wherein the automatically defining the contrast agent protocol is based on a model describing circulatory parameters of the object under examination.

10. The method of claim 9, wherein the model is based on a flow rate of blood changing as a function of an anatomical position and a diameter of blood vessels through which blood flows.

11. The method of claim 1, wherein the medical imaging method includes a magnetic resonance imaging method or a computed tomography method.

12. The method of claim 11, wherein the automatically defining the contrast agent protocol includes a definition of a flow rate of a injected contrast agent as a function of time, a definition of a concentration of a injected contrast agent as a function of time, or both a definition of a flow rate of a injected contrast agent as a function of time and a definition of a concentration of a injected contrast agent as a-function of time.

13. The method of claim 11, wherein the automatically defining the contrast agent protocol is based on a model describing circulatory parameters of the object under examination.

14. The method of claim 13, wherein the model is based on flow rate of blood changing as a function of an anatomical position and a diameter of blood vessels through which blood flows.

15. A memory device of a control device of an imaging medicinal system, storing a computer program including program segments to carry out the method of claim 11 when the computer program is executed in the control device of the imaging medicinal system.

16. A non-transitory computer readable medium including stored program segments, readable-in and executable by a computing unit, to carry out the method of claim 11 when the program segments are executed by the computing unit.

17. A memory device of a control device of an imaging medicinal system, storing a computer program including program segments to carry out the method of claim 1 when the computer program is executed in the control device of the imaging medicinal system.

18. A non-transitory computer readable medium including stored program segments, readable-in and executable by a computing unit, to carry out the method of claim 1 when the program segments are executed by the computing unit.

19. An imaging method, the method comprising:
using the method of claim 1 to determine the contrast agent protocol; and
performing imaging, via the contrast agent-enhanced medical imaging method, using the determined contrast agent protocol.

20. The imaging method of claim 19, further comprising:
sending a control signal for controlling a contrast agent injection to a contrast agent injection device after determining the contrast agent protocol.

21. The imaging method of claim 19, wherein the imaging includes a contrast agent-enhanced depiction of region of interest to be imaged of the object under examination.

22. A contrast agent protocol determination device for automatically defining a contrast agent protocol for a contrast agent-enhanced medical imaging method comprising:
a non-transitory memory having computer-readable instructions stored thereon;
and
at least one processor configured to execute the computer-readable instructions to cause the contrast agent protocol determination device to
acquire raw data, prior to injecting a contrast agent, for an overview recording of a region of interest of an object under examination via a medical imaging device;

reconstruct image data from the acquired raw data;
define an image recording protocol including a plurality of recording parameters including at least a scan rate of the medical imaging device based on the image data;
determine, prior to injecting the contrast agent, recording time points for a plurality of z-positions of the region of interest;
assign structures to the determined recording time points prior to injecting the contrast agent, the structures being acquired from the overview recording, the structures including at least one of an organ and a blood vessel; and
automatically define, prior to injecting the contrast agent, the contrast agent protocol, including syncing administering the contrast agent as a function of the scan rate, the acquired structures and respectively assigned recording time points to the assigned structures, wherein the contrast agent protocol including a temporal course of a contrast agent injection curve is defined as the function of the acquired structures and assigned recording time points.

23. An imaging medicinal device, comprising:
the contrast agent protocol determination device of claim 22.

24. The imaging medicinal device of claim 23, wherein the imaging medicinal device comprises a computed tomography system.

* * * * *